US010126269B2

(12) United States Patent
Bueno et al.

(10) Patent No.: US 10,126,269 B2
(45) Date of Patent: Nov. 13, 2018

(54) SYSTEM AND METHOD FOR INSPECTING FASTENERS

(71) Applicant: General Electric Company, Schenectady, NY (US)

(72) Inventors: Manuel Kenneth Bueno, Syracuse, NY (US); Willis James Perry, Lewistown, PA (US); Robert Charles Shaffer, Reedsville, PA (US)

(73) Assignee: General Electric Company, Schenectady, NY (US)

( * ) Notice: Subject to any disclaimer, the term of this patent is extended or adjusted under 35 U.S.C. 154(b) by 250 days.

(21) Appl. No.: 14/846,238

(22) Filed: Sep. 4, 2015

(65) Prior Publication Data

US 2016/0069838 A1 Mar. 10, 2016

Related U.S. Application Data

(60) Provisional application No. 62/046,678, filed on Sep. 5, 2014.

(51) Int. Cl.
*G01N 29/04* (2006.01)
*G01N 29/26* (2006.01)
*G01N 29/44* (2006.01)

(52) U.S. Cl.
CPC ......... *G01N 29/043* (2013.01); *G01N 29/262* (2013.01); *G01N 29/4427* (2013.01); *G01N 2291/044* (2013.01); *G01N 2291/106* (2013.01); *G01N 2291/2691* (2013.01)

(58) Field of Classification Search
CPC ............... G01N 29/043; G01N 29/262; G01N 29/4427; G01N 2291/106; G01N 2291/2691; G01N 2291/044
See application file for complete search history.

(56) References Cited

U.S. PATENT DOCUMENTS

| 3,977,236 | A | * | 8/1976 | Raatz, Jr. | ........... G01N 29/0645 73/614 |
|---|---|---|---|---|---|
| 5,859,370 | A | | 1/1999 | Suh et al. | |
| 7,017,414 | B2 | | 3/2006 | Falsetti et al. | |
| 7,328,619 | B2 | | 2/2008 | Moles et al. | |
| 8,434,216 | B2 | | 5/2013 | Mall et al. | |
| 2004/0065154 | A1 | * | 4/2004 | Kibblewhite | ........ G01N 29/048 73/761 |
| 2014/0283612 | A1 | * | 9/2014 | Williams | ............... G01N 29/24 73/633 |
| 2015/0260592 | A1 | * | 9/2015 | George | .................. G01L 5/243 73/629 |

* cited by examiner

*Primary Examiner* — Peter Macchiarolo
*Assistant Examiner* — Xin Zhong
(74) *Attorney, Agent, or Firm* — Mintz Levin Cohn Ferris Glovsky and Popeo, P.C.

(57) ABSTRACT

A fastener probe assembly includes a disc configured to rotate about a first axis of a fastener, an ultrasound probe coupled to the disc, and an encoder configured to determine an orientation of the ultrasound probe relative to the first axis of the fastener during an inspection of the fastener. The ultrasound probe is configured to interface with an axial end of the fastener, to emit ultrasound signals into the axial end of the fastener, and to receive ultrasound signals from the fastener.

20 Claims, 9 Drawing Sheets

SYSTEM AND METHOD FOR INSPECTING FASTENERS

CROSS REFERENCE TO RELATED APPLICATION

This application claims priority from and the benefit of U.S. Provisional Application Ser. No. 62/046,678, entitled "SYSTEM AND METHOD FOR INSPECTING FLANGE FASTENERS", filed Sep. 5, 2014, which is hereby incorporated by reference in its entirety.

BACKGROUND

The subject matter disclosed herein relates to non-destructive inspection, and more specifically to a system and method for inspection of fasteners of a hydrocarbon extraction system.

Components of the hydrocarbon extraction systems may be located in onshore, offshore, subsea, or subterranean environments. Hydrocarbon extraction systems convey various fluids between components via tubular members. The conveyed fluids may be pressurized relative to the external environment of the components or other tubular members. Some components of the hydrocarbon extraction system are coupled to one another via flange connections. The components and flange connections are subjected to various loads and environmental conditions during operation in the hydrocarbon extraction system. Some components may be utilized with another hydrocarbon extraction system if the components pass an inspection and satisfy known standards. Unfortunately, traditional inspection methods involve disassembling components and flange connections, which can be expensive and time consuming. Additionally, repeated assembly and disassembly may increase wear on components and the flange connections.

BRIEF DESCRIPTION

Certain embodiments commensurate in scope with the present disclosure are summarized below. These embodiments are not intended to limit the scope of the claim, but rather these embodiments are intended only to provide a brief summary of the present disclosure. Indeed, embodiments of the present disclosure may encompass a variety of forms that may be similar to or different from the embodiments set forth below.

In a first embodiment, a fastener probe assembly includes a disc configured to rotate about a first axis of a fastener, an ultrasound probe coupled to the disc, and an encoder configured to determine an orientation of the ultrasound probe relative to the first axis of the fastener during an inspection of the fastener. The ultrasound probe is configured to interface with an axial end of the fastener, to emit ultrasound signals into the axial end of the fastener, and to receive ultrasound signals from the fastener.

In another embodiment, a system includes a probe assembly and a controller coupled to the probe assembly. The probe assembly includes a housing and one or more probes. The probe assembly is configured to be coupled to a fastener of an assembled connection, and the housing is configured to at least partially receive an axial end of the fastener. The controller is configured to control an ultrasound inspection of the fastener. The ultrasound inspection includes emitting ultrasound signals from the one or more probes of the probe assembly into the axial end of the fastener, receiving ultrasound signals with the one or more probes of the probe assembly, and comparing the received ultrasound signals to baseline data for the fastener.

In another embodiment, an inspection method includes coupling a probe assembly to a fastener of an assembled connection of an assembled stack of components, emitting ultrasound signals from the fastener probe assembly into an axial end of the fastener, receiving ultrasound signals at the fastener probe assembly, and generating inspection data corresponding to the fastener based at least in part on the received ultrasound signals. The housing of the probe assembly is configured to at least partially receive the fastener. The received ultrasound signals are reflected from the fastener.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

Figure 1:
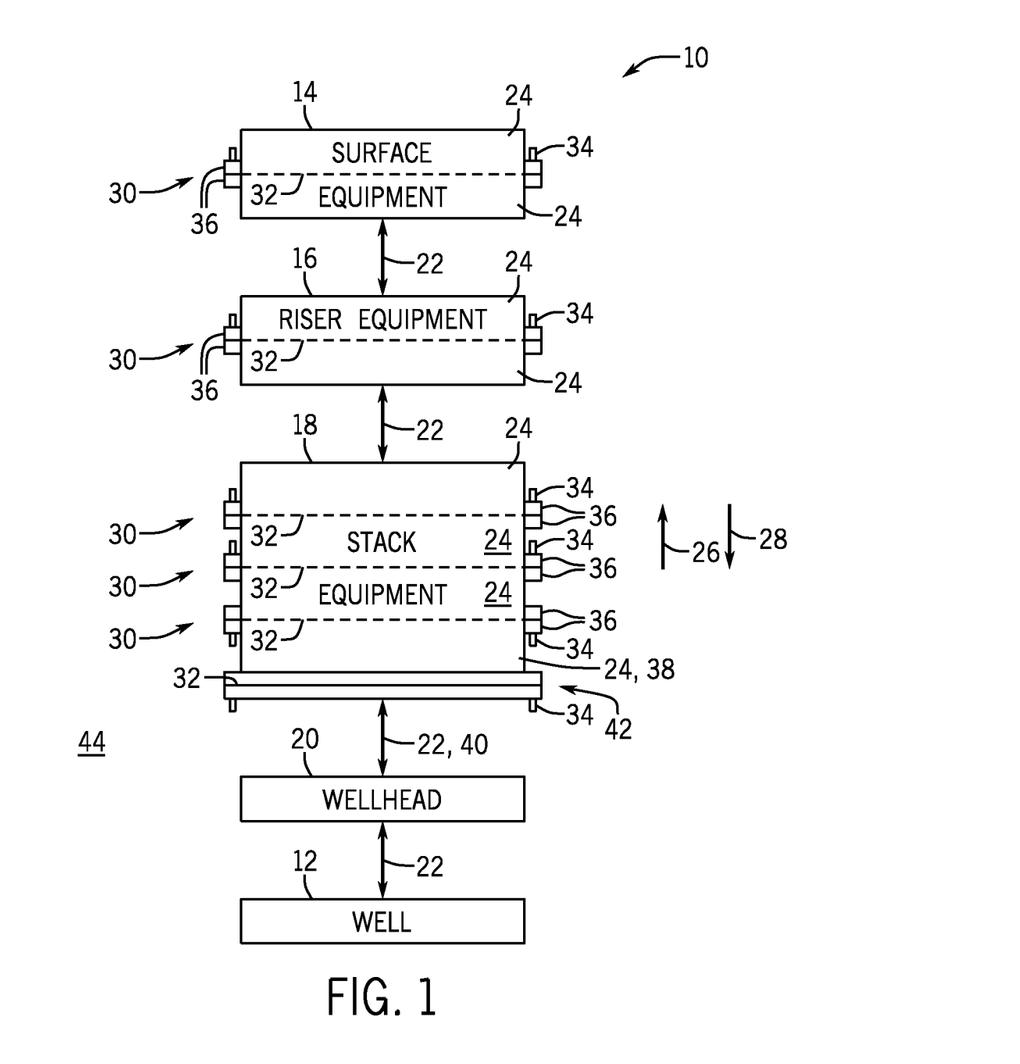
FIG. 1 is a block diagram of an embodiment of a hydrocarbon extraction system with some components coupled via flange connections.

A hydrocarbon extraction system 10 is illustrated in FIG. 1. The hydrocarbon extraction system 10 facilitates extraction of a hydrocarbon resource, such as oil or natural gas, from a well 12. The hydrocarbon extraction system 10 includes a variety of equipment, including surface equipment 14, riser equipment 16, and stack equipment 18, for extracting the resource from the well 12 via a wellhead 20. The hydrocarbon extraction system 10 may be employed in a variety of drilling or extraction applications, including onshore and offshore, i.e., subsea, drilling applications. For example, in a subsea resource extraction application, the surface equipment 14 is mounted to a drilling rig above the surface of the water, the stack equipment 18 is coupled to the wellhead 20 proximate to the sea floor, and the surface equipment 14 is coupled to the stack equipment 18 via the riser equipment 16. Connectors, illustrated by arrows 22, may facilitate coupling the equipment packages (e.g., surface equipment 14, riser equipment, 16, stack equipment 18, wellhead 20) of the hydrocarbon extraction system 10 to one another. Additionally, or in the alternative, connectors 22 may facilitate coupling of components within an equipment package to one another. Embodiments of the connector 22 may include, but are not limited to, an H-4® subsea connector, available from Vetco Gray of Houston, Tex.

The various equipment portions (e.g., surface equipment 14, riser equipment 16, stack equipment 18, wellhead 20) of the hydrocarbon extraction system 10 may include a variety of components 24. For example, the surface equipment 14 may include a variety of devices and systems, such as pumps, power supplies, cable and hose reels, control units, a diverter, a rotary table, and the like. Similarly, the riser equipment 16 may also include a variety of components, such as riser joints, valves, control units, and sensors, among others. In some embodiments, the riser equipment 16 may include a lower marine riser package (LMRP). The riser equipment 16 facilitates transmission of the extracted resource to the surface equipment 14 from the stack equipment 18 and the well 12. The stack equipment 18 also includes a number of components, such as one or more blowout preventers (BOPs), a subsea manifold, and/or production trees (e.g., completion or "Christmas" trees) for extracting the desired resource from the wellhead 20 and transmitting it to the surface equipment 14 and the riser equipment 16. The desired resource extracted from the wellhead 20 is transmitted to the surface equipment 14 generally in an upward direction 26. As utilized herein, a downward direction 28 is hereby defined as opposite the upward direction 26, such that the downward direction 28 is the general direction from the surface equipment 14 to the well 12. As may be appreciated, the upward direction 26 and the downward direction 28 are generally parallel to an axis of each component 24.

Some of the components 24 are coupled to one another via hydrocarbon component fasteners (e.g., flange connections 30), thereby forming flange seals 32 between the respective components 24. The flange connections 30 may secure the respective components 24 together via fasteners 34 that at least partially extend through flanges 36 of one or both components 24 of the flange connection 30. In some embodiments, a component 38 (e.g., blowout preventer) is coupled to a connector 40 (e.g., H-4® subsea connector) via a flange connection 42.

As may be appreciated, the desired resource extracted from the wellhead 20 is transferred in the upward direction 26 through the equipment of the hydrocarbon extraction system 10 such that the desired resource is isolated from the environment 44 (e.g., subsea environment). The flange seals 32 enable the desired resource to be isolated from the environment 44 at each flange connection 30. For example, the flange seals 32 facilitate the isolation of the desired resource at a high temperature and/or a high pressure relative to the environment 44.

Some components 24 of the hydrocarbon extraction system 10 may be utilized in other hydrocarbon extraction systems during the serviceable life of the respective components 24. For example, upon completion of use of the stack equipment 18 in a first hydrocarbon extraction system 10 at a first well 12, at least some of the components 24 of the stack equipment 18 may be utilized in a second hydrocarbon extraction system at a second well. Traditionally, the components of the stack equipment 18 are brought to the surface (e.g., oil rig, surface vessel) so that the components 24 may be disassembled from one another for inspection and/or certification for additional service. The inspection may be performed at a site remote from the hydrocarbon extraction system 10 and the wellhead 20. Traditional inspections of the components 24 may include penetrant testing and/or magnetic particle testing of the flanges 36, the flange seals 32, and the fasteners 34. As may be appreciated, disassembly of the flange connections 30 may be time consuming. Additionally, disassembly and reassembly of the flange connections 30 may increase wear on the flange seals 32, the fasteners 34, and the flanges 36 of the components 24.

Figure 2:
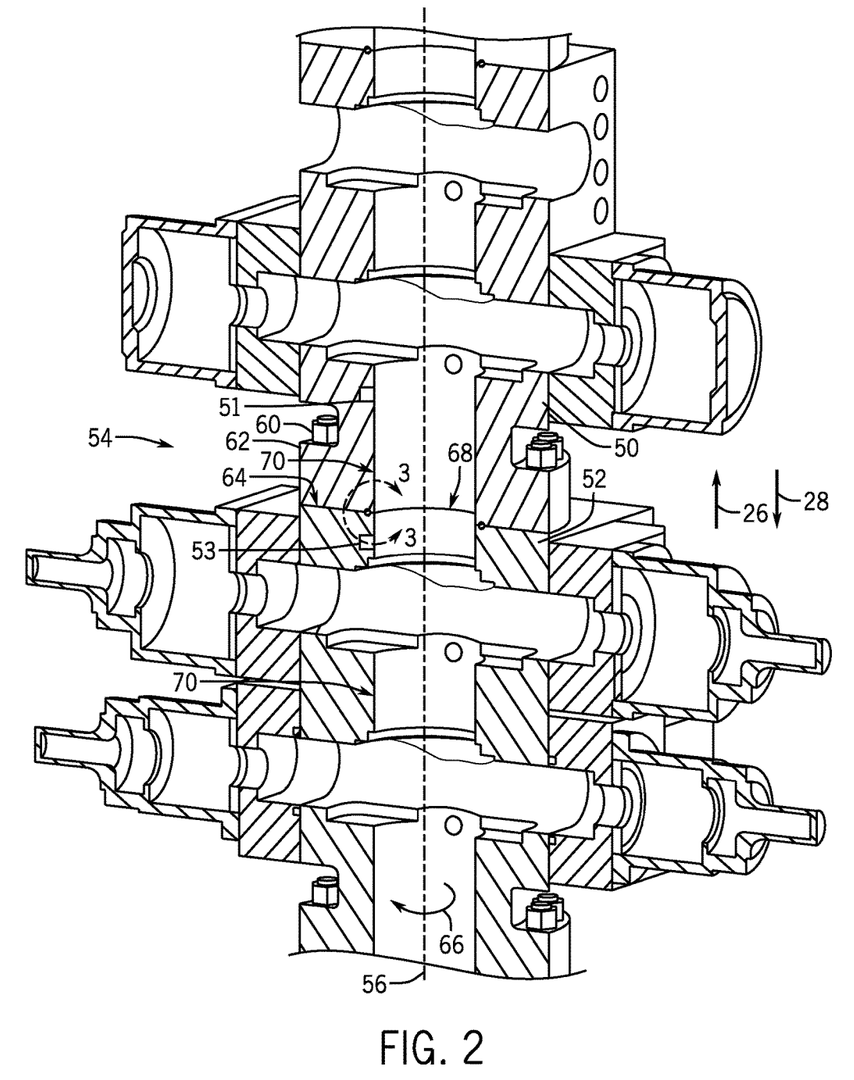
FIG. 2 is a cross-sectional view of an embodiment of a stack of a hydrocarbon extraction system with flange connections.

FIG. 2 is cross-sectional view of an embodiment of a portion of the stack equipment 18 of the hydrocarbon extraction system 10 of FIG. 1. A first component 50 of the stack equipment 18 is coupled to a second component 52 (e.g., blow out preventer (BOP)) via a flange connection 54. Both the first component 50 and the second component 52 are disposed about an axis 56 through a bore 58. In some embodiments, the first component 50 may be identified by a first identifier 51, and the second component 52 may be identified by a second identifier 53. The first and second identifiers 51, 53 may include, but are not limited to, serial numbers, bar codes, radio frequency identification (RFID) tags or chips, distinguishing part geometries, or any combination thereof. In some embodiments, the first and second identifiers 51, 53 are embedded within the respective components 50, 52.

The bore 58 facilitates fluid communication between the wellhead 20 and the surface equipment 14, such as for hydrocarbon flows, mud, or hydraulic fluids. A plurality of fasteners 60 (e.g., bolts, studs) extend through a flange 62 of the first component 52 and couple with a second surface 64 of the second component 52. The flange 62 extends in a circumferential direction 66 about the bore 58, and the plurality of fasteners 60 are disposed circumferentially about the axis 56 to secure the first component 50 to the second component 52. That is, the plurality of fasteners 60 may urge the first component 50 and the second component 52 towards each other such that a first surface 68 of the first component 50 interfaces with the second surface 64 of the second component 52.

Figure 3:
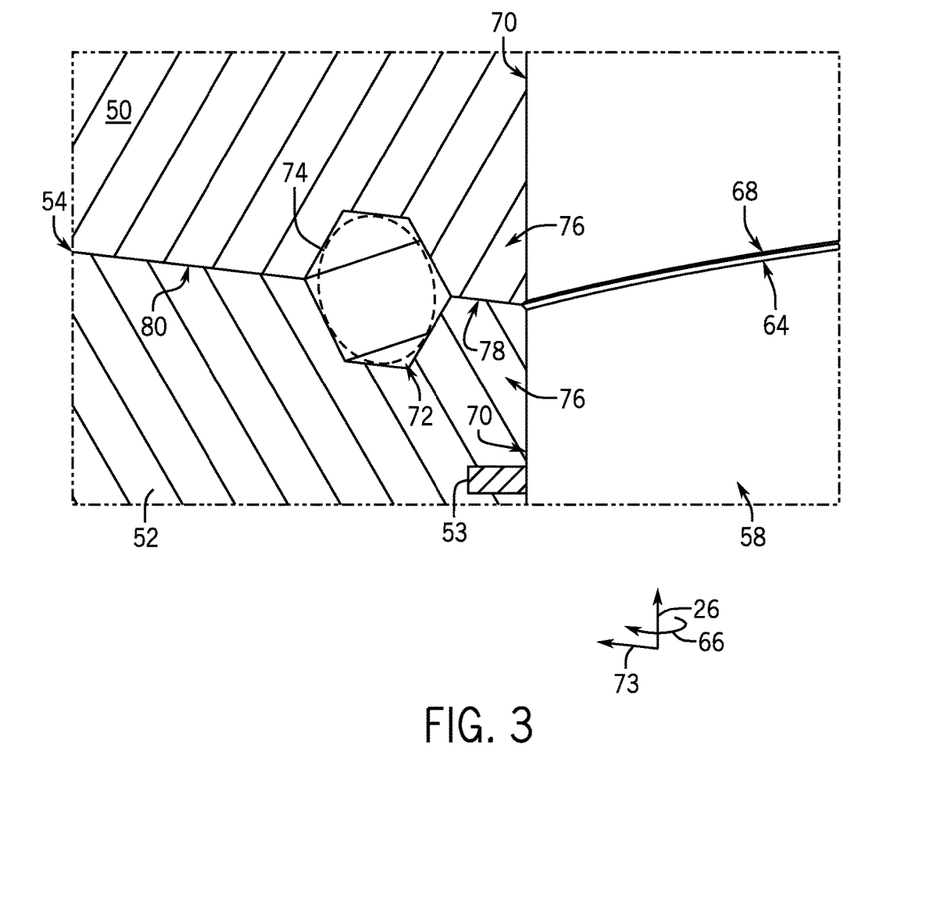
FIG. 3 is a cross-sectional view of an embodiment of a flange seal of a flange connection, taken along line 3-3 of FIG. 2.

FIG. 3 is a cross-sectional view of an embodiment of the flange connection 54 between the first component 50 and the second component 52, taken along line 3-3 of FIG. 2. Interior surfaces 70 of the first and second components 50, 52 form the bore 58 through the respective components 50, 52 of the assembled stack equipment 18. The first and second components 50, 52 may form a seal passage 72 near the interior surfaces 70 (e.g., around the bore 58) that extends in the circumferential direction 66 about the interior surfaces 70. The seal passage 72 is disposed in a radial direction 73 outside the interior surfaces 70. Recesses, grooves, or depressions in the first component 50 and/or the second component 52 form the seal passage 72. The shape of the seal passage 72 may include, but is not limited to a circle, a semicircle, an ellipse, a rectangle, a pentagon, a hexagon, an octagon, and so forth. The seal passage 72 is configured to receive a seal 74, such as an elastomeric seal, O-ring, C-ring (gasket), and so forth. As may be appreciated, the seal 74 provides flexibility to the flange connection 54 that enables fluids (e.g., hydrocarbons, oils, gases, slurries) within the bore 58 to remain isolated from the external environment 44 about the components 50, 52 despite some relative movement between the first and second components 50, 52 in the circumferential direction 66, the radial direction 73, or the axial 104. FIG. 3 illustrates an embodiment of the seal 74 with the dashed cross-section of a circular seal (e.g., O-ring). A lip portion 76 is radially disposed between the seal passage 72 and the interior surfaces 70 about the bore 58. The lip portion 76 may include portions of the first component 50 and the second component 52. Additionally, or in the alternative, the lip portion 76 may only include portions of the first component 50, or may only include portions of the second component 52. A lip interface 78 between the first surface 68 and the second surface 64 at the lip portion 76 facilitates the isolation of the bore 58 from the seal passage 72, and a body interface 80 facilitates the isolation of the seal passage 72 and the bore 58 from the external environment 44.

Various factors may affect the integrity and effectiveness of the flange connection 54 to isolate the bore 58 from the external environment 44 and to secure the first component 50 to the second component 52. The desired strength of portions of the first and second components 50, 52 is based at least in part on operating conditions of the hydrocarbon extraction system. The operating conditions may include, but are not limited to, the composition of the extracted resource, the pressure of the extracted resource, the external environment, the depth of the component when installed, and so forth. The strength of a component may be affected by flaws of the interior surfaces 70, the lip portion 76, the seal passage 76, the seal 74, or any combination thereof. Flaws may include, but are not limited to porosity, cracks (e.g., surface cracks or subsurface cracks), wear, or any combination thereof. Additionally, or in the alternative, flaws may affect the pressures at which the flange connection 54 between the first and second components 50, 52 forms an effective seal to isolate the bore 58 from the seal passage 72 and/or the external environment 44. Furthermore, flaws in the fasteners 60 of the flange connection 54 may affect the magnitude and the distribution about the axis 56 of a sealing force between the first component 50 and the second component 52.

The first and second components 50, 52 may be inspected and/or certified prior to utilization in a hydrocarbon extraction system 10. For example, the first and second components 50, 52 may be inspected and/or certified after manufacture and prior to installation in a first hydrocarbon extraction system. After utilization of the first and second components 50, 52 in the first hydrocarbon extraction system, it may be desirable for the first and second components 50, 52 to be installed in a second hydrocarbon extraction system. However, standards or regulations may require re-inspection and/or re-certification of the first and second components 50, 52 before utilization in the second hydrocarbon extraction system. For example, re-inspection and/or re-certification may identify flaws (e.g., porosity, cracks, wear) of portions of the first and second components 50, 52. Systems and methods described herein facilitate inspection of portions of the first and second components 50, 52 while the first and second components 50, 52 are assembled without disassembly of the flange connection 54. For example, a probe assembly discussed herein may utilize one or more ultrasound probes to inspect portions of the assembled first and second components 50, 52 of the flange connection 54. In some embodiments, probe assemblies may utilize one or more phased arrays of ultrasound probes. Accordingly, the probe assembly enables non-destructive testing of assembled flange connection 54, thereby reducing the cost, labor, and time of assembly and disassembly of the flange connection 54 with traditional inspection methods. Furthermore, a probe assembly may enable multiple components and multiple flange connections assembled together in series to be inspected at substantially the same time, thereby further reducing the cost, labor, and time of inspection.

Figure 4:
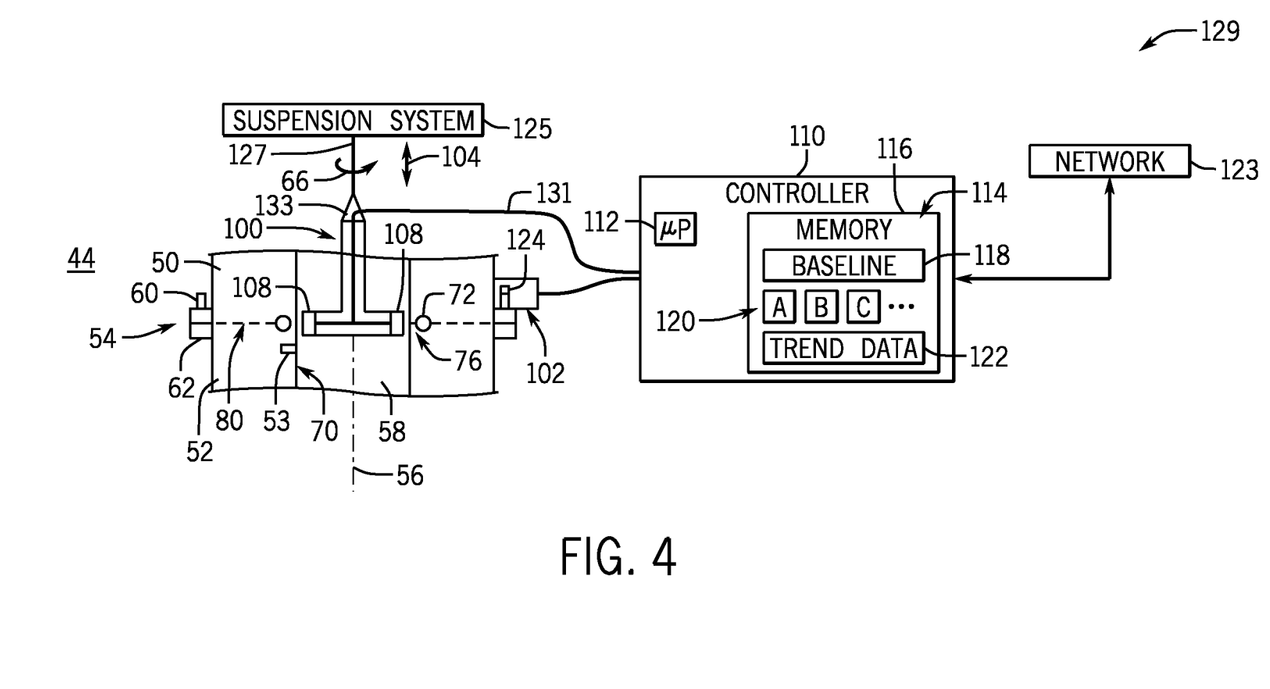
FIG. 4 is a block diagram of embodiments of probe assemblies and a flange connection.

FIG. 4 illustrates embodiments of a first probe assembly 100 (e.g., bore probe assembly, flange probe assembly) and a second probe assembly 102 (e.g., bolt probe assembly) that are configured to inspect portions of the first and second components 50, 52. The first probe assembly 100 is disposed within the bore 58 of the first and second components 50, 52 along the axis 56. The first probe assembly 100 is moved in an axial direction 104 along the bore 58 to inspect axial portions of the first and second components 50, 52, and the first probe assembly 100 is rotated in the circumferential direction 66 to inspect circumferential portions of the first and second components 50, 52. One or more probes 108 (e.g., ultrasound probes) coupled to a controller 110 obtain inspection data regarding portions of the first and second components 50, 52 adjacent to the one or more probes 108. The one or more probes 108 may be in contact with the interior surfaces 70 of the bore 58 to obtain the inspection data. In some embodiments, the one or more probes 108 emit ultrasound signals into the first and second components 50, 52, and the one or more probes 108 receive reflected ultrasound signals. Each probe 108 may include one or more transducers. A couplant medium (e.g., water, oil, lubricant) may be disposed between the one or more probes 108 and the interior surfaces 70 of the bore 58 such that the one or more probes 108 are in contact with the interior surfaces 70 via the couplant medium. The couplant medium may be applied (e.g., injected, pumped, sprayed) to the surface of the one or more probes 108, the interior surfaces 70 of the bore 58, or any combination thereof. The couplant medium may facilitate transmission of the ultrasound signals between the one or more probes 108 and the interior surfaces 70 of the first and second components 50, 52. The one or more probes 108 emit the ultrasound signals in the radial direction 73 into the first and second components 50, 52.

A processor 112 of the controller 110 may process signals based at least in part on the received signals to generate the inspection data 114 that may be stored in a memory 116. The inspection data 114 may include, but is not limited to baseline data 118, inspection run data 120, and trend data 122. The baseline data 118 may be used for comparison with later obtained inspection run data 120 to determine any deviations from a baseline (e.g., zero reference). The baseline data 118 may be based at least in part on a model, or the baseline data 118 may be empirically determined. For example, the baseline data 118 may be empirically determined from components 50, 52 of an assembled flange connection 54 after manufacture or refurbishment. The inspection run data 120 is based at least in part on signals processed by the processor 112 for a particular inspection run, such as a re-inspection prior to installation of the first and second components 50, 52 in a second hydrocarbon extraction system. The inspection run data 120 may be compared with the baseline data 118 to identify and evaluate any flaws (e.g., porosity, cracks, wear) of the components 50, 52. The processor 112 may generate the trend data 122 upon comparison of one or more sets of the inspection run data 120 with previously obtained sets of the inspection run data 120. In some embodiments, trend data 122 may be based at least in part on comparison of inspection run data 120 from different components, different hydrocarbon extraction systems, or any combination thereof. Accordingly, the trend data 122 may facilitate the identification of trends or patterns in cracks or wear of components of the hydrocarbon extraction system.

In some embodiments, the inspection data 114 may include identifying information regarding the inspected component (e.g., part number, flange connection identifier, RFID, installation history) and the inspection process (e.g., inspection operator, date, time). Furthermore, some of the inspection data 114 may be stored on and/or accessed from a network 123 remote from the controller 110. As may be appreciated, the network 123 may facilitate the communication of inspection data 114 between controllers 110 at different locations.

In some embodiments, a suspension system 125 coupled to the first probe assembly 100 moves the first probe assembly 100 in the axial direction 104 within the bore 58. The first probe assembly 100 may be suspended by one or more cables 127 coupled to the suspension system 125. In some embodiments, the suspension system 125 includes one or more winches or pulleys coupled to the one or more cables 127 to facilitate movement in the axial direction 104. The suspension system 125 may couple to the stack equipment 18 such that the one or more cables 127 are suspended proximate to the axis 56 of the bore 58. One or more umbilical lines 131 couple the first probe assembly 100 to the controller 110. Each umbilical line of the one or more umbilical lines 131 may convey electrical signals, electrical power, or fluids between the controller 110 and the first probe assembly 100. A connection receiver 133 of the first probe assembly 100 may be configured to couple the one or more umbilical lines 131 with corresponding conduits of the first probe assembly 100 via one or more quick connections. While the suspension system 125 and the controller 110 are illustrated in FIG. 4 as separate components of an inspection system 129, it may be appreciated that some embodiments of the suspension system 125 may be integrated with the controller 110, such as being disposed within a common enclosure.

The second probe assembly 102 utilizes one or more fastener probes 124 to generate inspection data regarding the plurality of fasteners 60 of the flange connection 54. The one or more fastener probes 124 emit ultrasound signals into the fasteners 60 in the axial direction 104, and the one or more fastener probes 124 receive reflected ultrasound signals. In some embodiments, the one or more fastener probes 124 emit ultrasound signals in a direction substantially parallel (e.g., less than 30° offset) to the axial direction 104. As may be appreciated, the one or more fastener probes 124 may be in contact with a fastener 60 (e.g., bolt, stud) when emitting and receiving the ultrasound signals. The couplant medium (e.g., water, oil, lubricant) may be disposed between the one or more fastener probes 124 and the fastener 60 such that the one or more fastener probes 124 are in contact with the fastener 60 via the couplant medium. The couplant medium may be applied (e.g., injected, pumped, sprayed) to the surface of the one or more fastener probes 124, the fastener 60, or any combination thereof. The couplant medium may facilitate transmission of the ultrasound signals between the one or more fastener probes 124 and the fastener 60. In some embodiments, an operator that arranges (e.g., couples) the second probe assembly 102 to the fastener 60 may apply the couplant medium to the fastener 60. In a similar manner as discussed above with the one or more probes 108, the controller 110 may process signals based at least in part on the received signals to generate the inspection data 114 that may be stored in the memory 116. The inspection data 114 may be associated with each respective fastener 60 of the plurality of fasteners. As discussed in detail below, some embodiments of the fastener probe 124 of the second probe assembly 102 may rotate about a fastener axis to obtain the inspection data for each fastener 60. Accordingly, the inspection data 114 for each fastener 60 of the flange connection 54 may be obtained in series via the second probe assembly 102. Multiple second probe assemblies 102 may facilitate obtaining inspection data for multiple respective fasteners 60 in parallel with one another.

Figure 5:
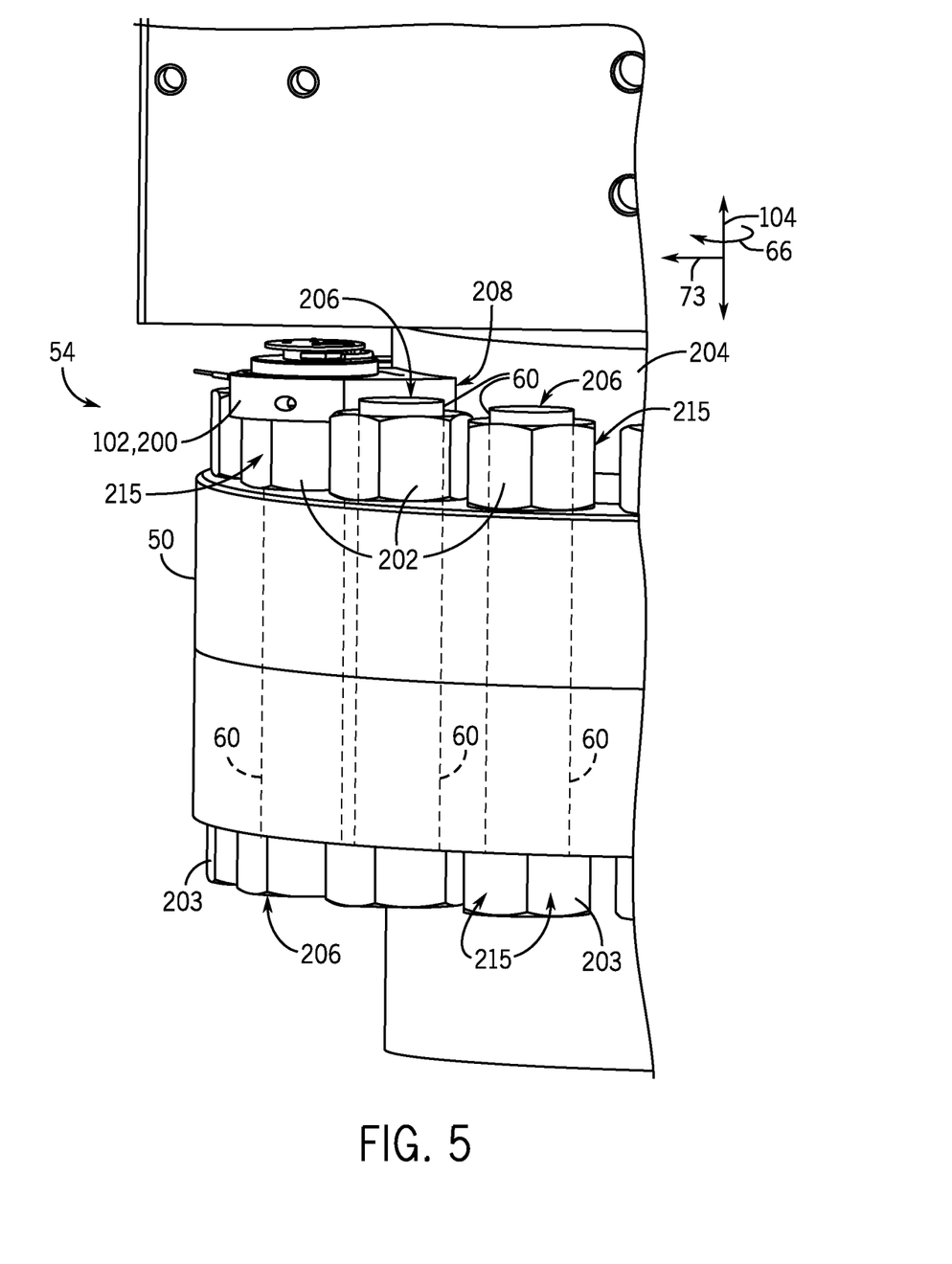
FIG. 5 is a perspective view of an embodiment of a fastener probe assembly and fastener studs of a flange connection.

FIG. 5 is perspective view of an embodiment of a second probe assembly 102 coupled to a fastener 60 of a flange connection 54. The second probe assembly 102 may be a fastener probe assembly 200 configured to at least partially receive the fastener 60 and inspect the fastener 60 from the axial direction 104. Each fastener 60 may be a bolt or stud that extends (e.g., axially) through the flange 62 of the first component 50 to couple with the second component 52, as shown by the dashed lines in FIG. 5. In some embodiments, the fasteners 60 are threadably coupled to, brazed, welded, or integrally formed with either the first component 50 or the second component 52. A nut 202 may be coupled (e.g., threadably coupled) to each fastener 60 to secure the flange 62 to the second component 52, thereby forming the flange connection 54. In some embodiments, the fastener probe assembly 200 is configured to at least partially receive the nut 202 coupled to each fastener 60. Additionally, or in the alternative, the fastener probe assembly 200 is configured to at least partially receive a bolt head 203 of each fastener 60, where it may be appreciated that the bolt head 203 at a first end of a fastener 60 may have substantially the same geometry (e.g., hexagonal) as the nut 202 coupled to an opposite second end of the fastener 60. The fasteners 60 are spaced apart in the radial direction 73 from a body 204 of the first component 50. Each fastener connection 54 may have approximately 4, 5, 6, 7, 8, 10, 12, 16, 18, 20, 24, 28, 36, or more fasteners 60 to couple the first component 50 to the second component 52.

The fastener probe assembly 200 is configured to couple with an axial end 206 of each fastener 60. In some embodiments, an orienting surface 208 of the fastener probe assembly 200 interfaces with the body 204 of the first component 50 when the fastener probe assembly 200 is coupled to the axial end 206 of a fastener 60. The orienting surface 208 may enable the fastener probe assembly 200 to be consistently aligned in the radial direction 73 relative to the axis 56 of the flange connection 54 when the fastener probe assembly 200 is coupled to each fastener 60.

Figure 6:
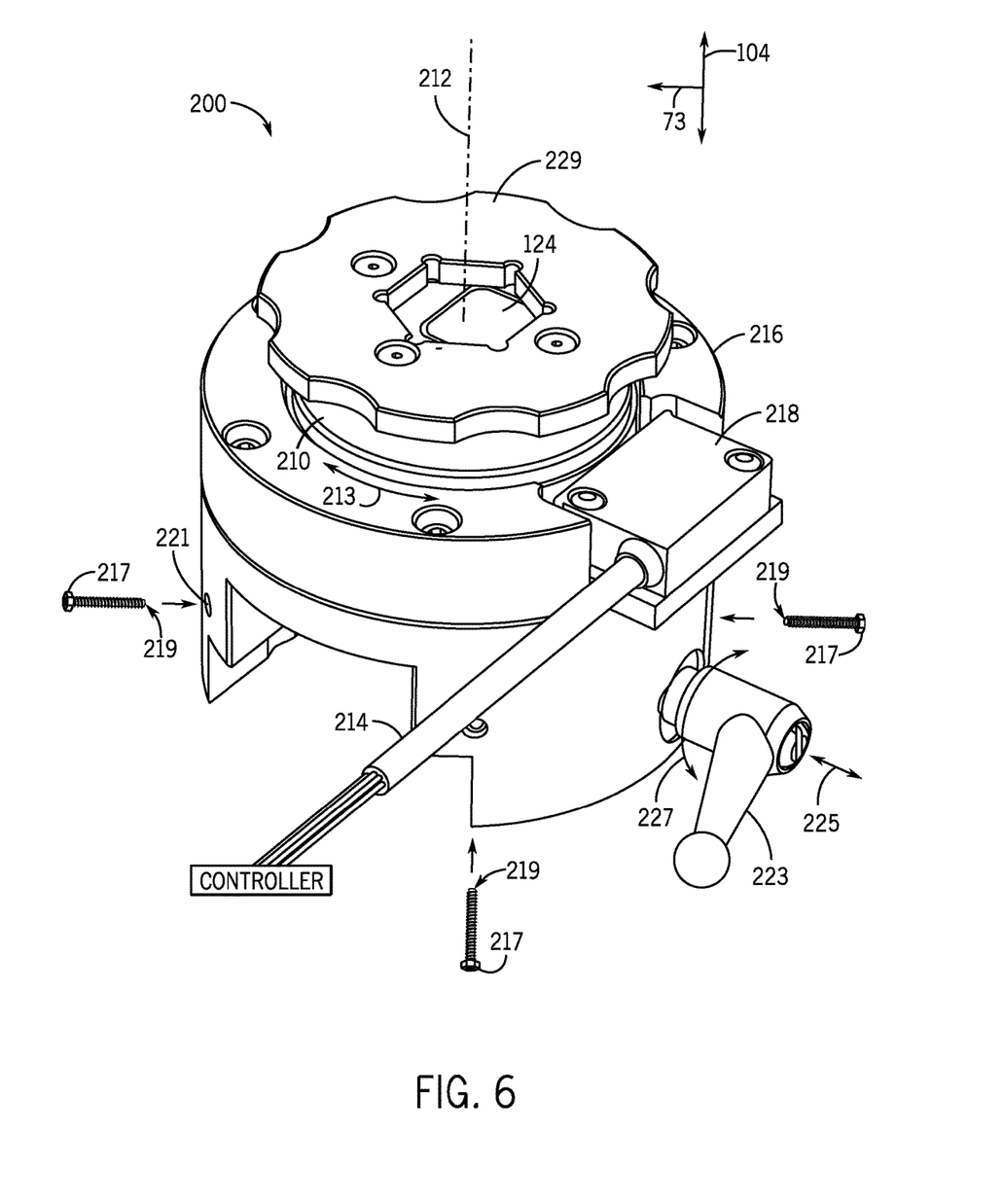
FIG. 6 is a perspective view of an embodiment of the fastener probe assembly.

FIG. 6 is a perspective top view of an embodiment of the fastener probe assembly 200. The fastener probe 124 is configured to emit ultrasound signals into the axial end 206 of each fastener 60. The fastener probe 124 is coupled to a disc 210 that rotates about a fastener axis 212, as shown by arrow 213. As the disc rotates 210, a cable 214 that couples the fastener probe 124 to the controller 110 may coil or uncoil within a housing 216. The housing 216 is configured to at least partially receive the fastener 60. For example, the housing 216 may be configured to interface with the driving surfaces 215 of the nut 202 or the bolt head 203 of the fastener 60 to maintain the orientation of the housing 216 about the fastener axis 212 when the fastener probe assembly 200 is coupled to the fastener 60. In some embodiments, multiple (e.g., 2, 3, 4, 5, 6, 7, 8, 9, 10, or more) fastener probes 124 are coupled to the disc 210. While the fastener probe 124 of the fastener probe assembly 200 illustrated in FIG. 6 emits ultrasound signals into and receives reflected ultrasound signals from the same axial end 206 of the fastener 60, other embodiments of the fastener probe assembly 200 may utilize separate transmitters and receivers at opposite ends of the fastener 60 for through transmission of the ultrasound signals through the fastener 60.

An encoder (e.g., rotary encoder) 218 coupled to the disc 210 and to the controller 110 enables the controller 110 to determine the circumferential position of the one or more fastener probes 124 about the fastener axis 212 as the disc 210 rotates during a fastener inspection. In some embodiments, the rotary encoder is a magnetic band ring encoder. Accordingly, the encoder 218 and the inspection data enables the controller 110 to identify the circumferential and axial location of any flaws (e.g., porosity, cracks, wear) identified in the fasteners 60. In some embodiments, one or more pins 217 (e.g., spring ball plungers) of the housing 216 may radially interface with the nut 202 or bolt head 203 of the fastener 60 when the fastener probe assembly 200 is coupled to the fastener 60. Ends 219 of the pins 217 (e.g., spring ball plungers) may be biased into contact with the fastener 60, thereby centering the one or more fastener probes 124 about the fastener axis 212. FIG. 6 illustrates the one or more biased pins 217 (e.g., spring ball plungers) as external to the housing 216, however, the one or more biased pins may be installed within the housing 216 through retention recesses 221 that may extend through the housing 216. A lock feature 223 may move in a radial direction 225 to interface with the nut 202 or bolt head 203 of the fastener 60 and maintain the orientation of the housing 216 relative to the fastener 60. In some embodiments, the lock feature 223 is a lever, such that rotation in a direction 227 about the radial direction 225 engages or disengages the lock feature 223 with the fastener 60, thereby maintaining the orientation of the housing 216 relative to the fastener 60. A cover 229 may be positioned over the one or more fastener probes 124 to protect the one or more probes 124 from unintended physical contact with the environment. Moreover, the cover 229 may facilitate manual positioning of the fastener probe assembly 200 on the fastener 60 to be inspected.

In some embodiments as illustrated in FIG. 5, the orienting surface 208 interfaces with the body 204 of the first component 50 so that the fastener probe assembly 200 may start the inspection of each fastener 60 from substantially the same orientation and position relative to the axis 56. Thus, the rotary encoder 218 may facilitate the determination of the position of the fastener probe 124 relative to the fastener axis 212 for each fastener 60, and the orienting surface 208 facilitates the determination of the position of the fastener probe assembly 200 relative to the axis 56 of the flange connection 54. Inspection of each fastener in a similar manner with the fastener probe assembly 200 and the fastener probe 124 in consistent orientations for each fastener 60 enables the inspection data for each fastener 60 to be readily compared with one another.

Figure 7:
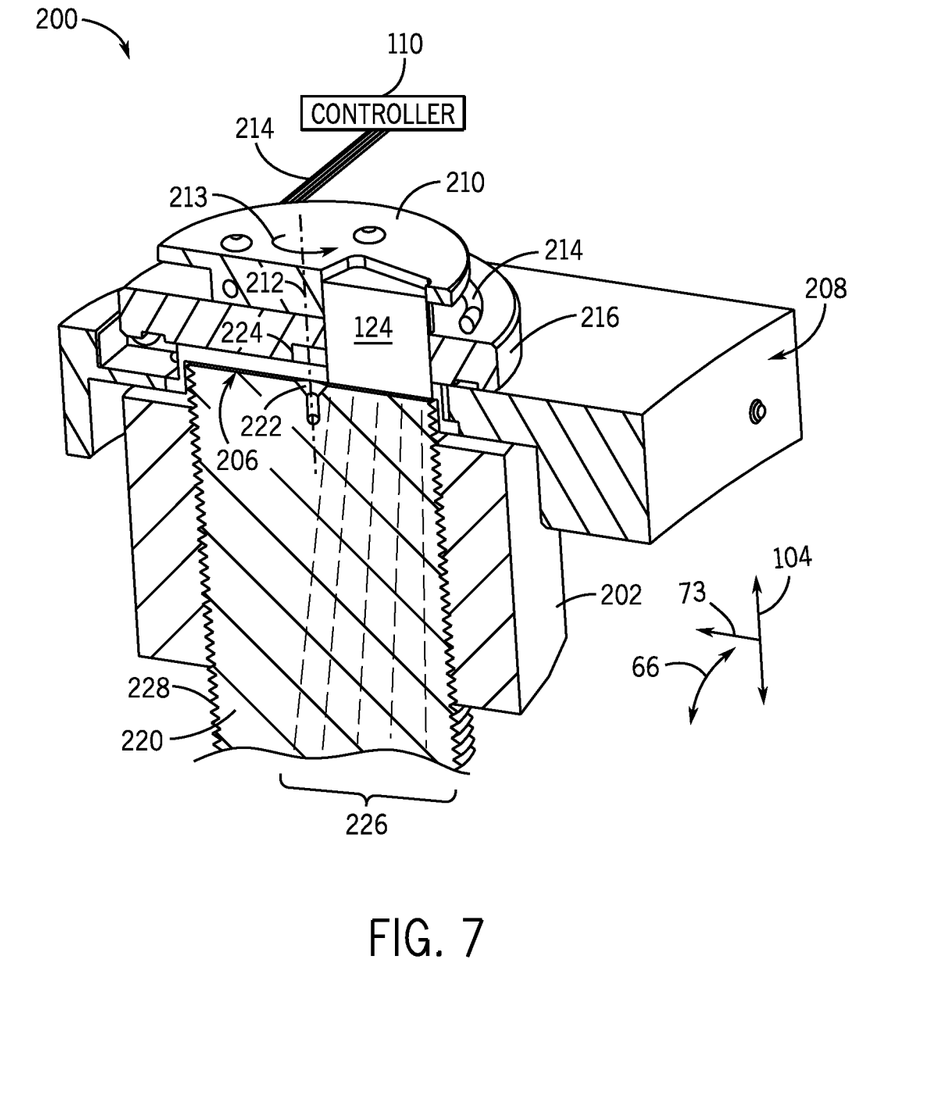
FIG. 7 is a cross-sectional view of an embodiment of the fastener probe assembly and a fastener.

Identification of each fastener 60 may aid the comparison of inspection data for each fastener 60 to other fasteners 60 of the flange connection 54. Additionally, identification of each fastener 60 may enable the comparison of inspection data for each fastener 60 to itself over a service life of the respective fastener 60. FIG. 7 is a cross-sectional view of an embodiment of the fastener probe assembly 200 and a fastener 220 with an identifier 222. The identifier 222 may include, but is not limited to a bar code, a part number, a unique geometry, an RFID tag or chip, or any combination thereof. In some embodiments, a sensor (e.g., scanner, chip reader) 224 of the fastener probe assembly 200 may determine the identity of the fastener 220 via the identifier 222. The identifier 222 may be disposed in a centering feature of the fastener 220 along the fastener axis 212. In some embodiments, the fastener probe 124 is arranged eccentrically in the disc 210 about the fastener axis 212 so that the fastener probe 124 does not emit ultrasound signals directly through the identifier 222.

Figure 8:
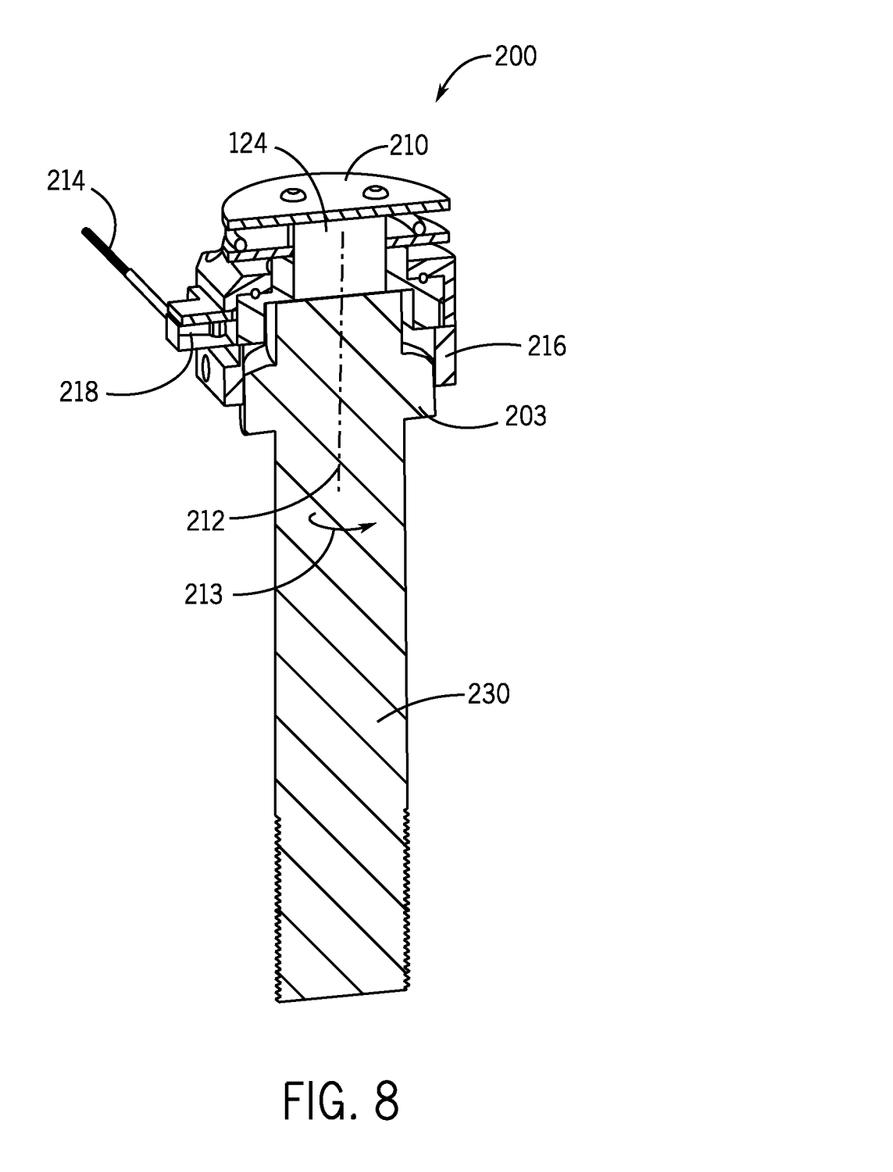
FIG. 8 is a cross-sectional view of an embodiment of a fastener probe assembly and a fastener bolt of a flange connection.

Mounted eccentrically about the fastener axis 212, the fastener probe 124 emits ultrasound signals through a section of the fastener 220, as shown by the lines 226. FIG. 8 is a cross-sectional view of an embodiment of a fastener probe assembly 200 with the fastener probe 124 mounted to the disc 210 concentric with the fastener axis 212. For example, FIG. 8 illustrates the fastener probe assembly 200 coupled to a fastener 230 (e.g., bolt) of an H-4® subsea connector without an identifier 222 embedded in along the fastener axis 212. Rotation of the discs 210 about the fastener axes 212 illustrated in FIGS. 7 and 8 sweeps the ultrasound signals through substantially the entire respective fastener 220, 230. The controller 110 may control the movement of the disc 210 in direction 213 about the fastener axis 212 based at least in part on feedback from the encoder 218.

In some embodiments, the fastener probe 124 is a phased array of ultrasound transducers controlled by the controller 110. The controller 110 may control the phased array fastener probe 124 to adjust the coverage depth and/or the resolution of the ultrasound signals to identify flaws (e.g., porosity, cracks, wear) of the fastener 220, 230. In particular, the fastener probe 124 may be controlled to identify and evaluate flaws in threads 228 of the fastener 220, 230.

Figure 9:
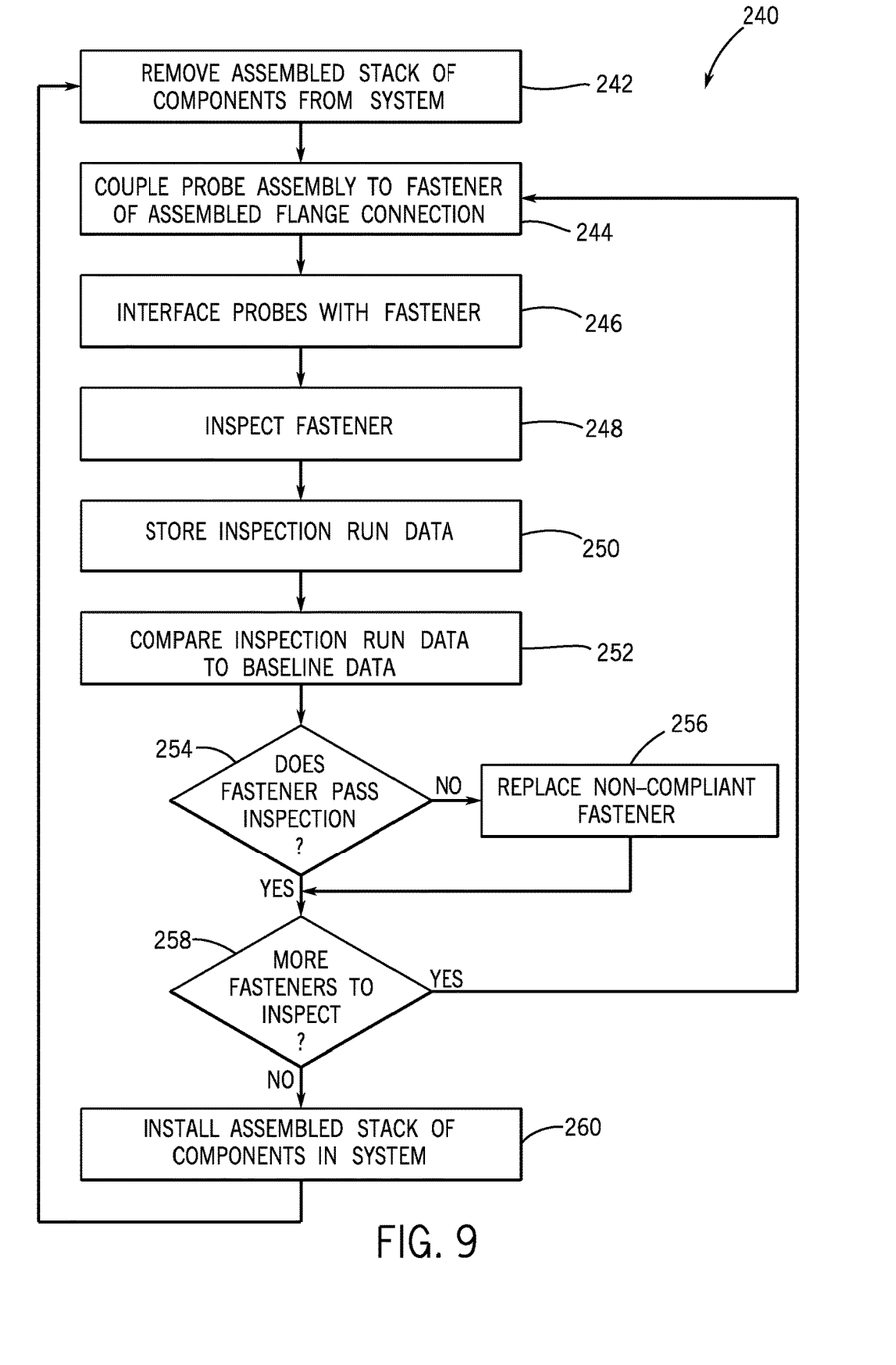
FIG. 9 is an embodiment of a method for inspecting fasteners of an assembled flange connection.

FIG. 9 is an embodiment of a method 240 for inspecting fasteners of an assembled flange connection of an assembled stack of components. The assembled stack of components is removed (block 242) from a system (e.g., hydrocarbon extraction system). The assembled stack may include two or more components coupled to one another via a flange connection as discussed above. For example, components of the assembled stack may include, but are not limited to, a lower marine riser package, one or more blowout preventers (BOPs), a subsea manifold, production trees, an H-4® subsea connector, or any combination thereof. In some embodiments, the assembled stack is removed from a subsea environment to the surface of a drilling rig or a ship. Once removed from the system, the fastener probe assembly is coupled (block 244) to a fastener (e.g., body, bolt head, nut) of an assembled flange connection. As discussed above, the couplant medium may be applied to the fastener when the fastener probe assembly is coupled (block 244) to the fastener, such that the one or more probes of the fastener probe assembly are in contact with the fastener via the couplant medium. Coupling the fastener probe assembly may orient the fastener probe assembly in a consistent orientation relative to the axis of the assembled flange connection. Additionally, the fastener probes of the fastener probe assembly are interfaced (block 246) with the fastener to be inspected. For example, the fastener probes interface with an axial end of the fastener. As discussed above, the fastener probes may include, but are not limited to ultrasound probes that are configured to emit and receive ultrasound signals. Moreover, each of the one or more ultrasound probes may be a phased array of ultrasound transducers.

The fastener probe is moved about the axis of the fastener while emitting ultrasound signal to inspect (block 248) the fastener. As discussed herein, the fastener probe assembly is configured to inspect each fastener of a flange connection without previously disassembling the fastener from the flange connection. The controller coupled to the fastener probe assembly stores (block 250) the inspection run data generated during the inspection (block 248). The stored inspection data may identify features of portions of the fastener of the inspected flange connection. The controller may compare (block 252) the inspection run data to baseline data. The comparison may enable the controller or an operator to determine (node 254) whether the fastener passes inspection. If the fastener does not pass inspection, the non-compliant fastener may be replaced (block 256). If the fastener does pass inspection or the fastener is replaced, then the controller or the operator determined (node 258) whether there are more fasteners of the flange connection to be inspected. As discussed above, each flange connection may have 4, 8, 12, 24, 36, or more fasteners, and the fasteners may be inspected in series or in parallel. If there are more fasteners to inspect, then the fastener probe assembly is coupled (block 244) to another fastener that has not yet been inspected. If there are no more fasteners to be inspected, then the assembled stack of components with the inspected fasteners of the flange connection may be installed (block 260) into another system.

Traditionally, the components of a flange connection are disassembled and each of the fasteners is removed for penetrant or magnetic particle inspection. Accordingly, the method 240 enables the inspection of fasteners of a flange connection without previously disassembling the flange connection, thereby reducing the inspection time and inspection costs. The fasteners that pass inspection are not removed from the flange connection. In some embodiments, only fasteners that do not pass the inspection are removed from the flange connection. Moreover, inspecting the fasteners of assembled flange connections may reduce the wear on the fasteners from unnecessarily disassembly and reassembly.

This written description uses examples to disclose the embodiments, including the best mode, and also to enable any person skilled in the art to practice the present disclosure, including making and using any devices or systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A fastener probe assembly comprising:
   a housing configured to interface with driving surfaces of a nut about a fastener or a bolt head of the fastener to maintain an orientation of the housing relative to the fastener, wherein the housing is configured to at least partially receive an axial end of the fastener;
   a disc disposed within the housing, wherein the disc is configured to rotate about a first axis of the fastener;
   an ultrasound probe fixedly mounted to a lower portion of the disc, wherein the ultrasound probe is configured to interface with the axial end of the fastener, to emit ultrasound signals into the axial end of the fastener, and to receive ultrasound signals from the fastener; and
   an encoder configured to determine an orientation of the ultrasound probe relative to the first axis of the fastener during an inspection of the fastener.

2. The fastener probe assembly of claim 1, wherein the housing is configured to interface with the fastener to align the first axis of the fastener with a second axis of the disc.

3. The fastener probe assembly of claim 2, wherein the housing comprises a manual lock feature configured to maintain an orientation of the housing relative to the fastener.

4. The fastener probe assembly of claim 1, comprising a sensor configured to determine an identity of the fastener based at least in part on an identifier of the fastener.

5. The fastener probe assembly of claim 4, wherein the sensor is configured to detect a radio frequency identification tag corresponding to the identity of the fastener.

6. The fastener probe assembly of claim 1, wherein the ultrasound probe is eccentrically mounted to the disc and the ultrasound probe is configured to eccentrically rotate about the first axis.

7. The fastener probe assembly of claim 1, comprising a controller configured to control the rotation of the disc about the first axis of the fastener.

8. The fastener probe assembly of claim 7, wherein the controller is configured to identify flaws in the fastener based at least in part on the received ultrasound signals.

9. The fastener probe assembly of claim 1, wherein the ultrasound probe comprises a phased array of ultrasound transducers coupled to the disc.

10. The fastener probe assembly of claim 1, comprising a second ultrasound probe coupled to the disc, wherein the second ultrasound probe is configured to interface with the axial end of the fastener, to emit second ultrasound signals into the axial end of the fastener, and to receive second ultrasound signals from the fastener.

11. A system comprising:
    a probe assembly comprising a housing and one or more probes, wherein the probe assembly is configured to be coupled to a fastener of an assembled connection, the housing is configured to at least partially receive an axial end of the fastener, and the housing is configured to interface with driving surfaces of a nut about the fastener or a bolt head of the fastener to maintain an orientation of the housing relative to the fastener; and
    a controller coupled to the probe assembly, wherein the controller is configured to control an ultrasound inspection of the fastener, wherein the ultrasound inspection of the fastener comprises emitting ultrasound signals from the one or more probes of the probe assembly into the axial end of the fastener, receiving ultrasound signals with the one or more probes of the probe assembly, and comparing the received ultrasound signals to baseline data for the fastener,
    wherein the one or more probes are fixedly mounted to a lower portion of a disc disposed within the housing, the disc configured to rotate about an axis of the fastener.

12. The controller of claim 11, wherein the controller is configured to control a circumferential movement of the one or more probes of the probe assembly about an axis of the fastener.

13. The controller of claim 12, wherein the controller is configured to determine a location of a flaw within the fastener based at least in part on the received ultrasound signals and feedback from a rotary encoder, wherein the feedback from the rotary encoder is based on the circumferential movement of the one or more probes of the probe assembly.

14. The controller of claim 11, wherein the controller is configured to determine an identity of the fastener based at least in part on a radio frequency identification tag of the fastener.

15. An inspection method comprising:
coupling a probe assembly to a fastener of an assembled connection of an assembled stack of components, wherein a housing of the probe assembly is configured to at least partially receive the fastener, and the housing interfaces with driving surfaces of a nut about the fastener or a bolt head of the fastener to maintain an orientation of the housing relative to the fastener;
emitting ultrasound signals from the fastener probe assembly into an axial end of the fastener;
receiving ultrasound signals at the fastener probe assembly, wherein the received ultrasound signals are reflected from the fastener; and
generating inspection data corresponding to the fastener based at least in part on the received ultrasound signals, wherein the probe assembly includes one or more probes fixedly mounted to a lower portion of a disc disposed within the housing, the disc configured to rotate about an axis of the fastener.

16. The inspection method of claim 15, comprising rotating the probe assembly about an axis of the fastener while emitting the ultrasound signals from the fastener probe assembly and receiving the ultrasound signals at the fastener probe assembly.

17. The inspection method of claim 15, comprising determining an identity of the fastener based at least in part on a radio frequency identification tag of the fastener.

18. The inspection method of claim 15, comprising centering the housing of the probe assembly and the fastener probe assembly about an axis of the fastener, wherein centering the housing comprises at least one of:
interfacing biased pins with driving surfaces of the nut
interfacing biased pins with the bolt head of the fastener; and
engaging a lock feature.

19. The inspection method of claim 15, comprising identifying flaws in the fastener of the assembled connection based at least in part on the received ultrasound signals without disassembling the assembled connection.

20. The inspection method of claim 15, comprising certifying the assembled stack of components for installation in a hydrocarbon extraction system without disassembling the assembled flange connection.

* * * * *